United States Patent [19]
Watanabe et al.

[11] 3,971,832
[45] July 27, 1976

[54] PROCESS FOR PRODUCING ORTHO-METHYLPHENOLS

[75] Inventors: Yoshihisa Watanabe; Makoto Takeda; Makoto Imanari, all of Ami, Japan

[73] Assignee: Mitsubishi Petrochemical Company Limited, Japan

[22] Filed: Apr. 10, 1974

[21] Appl. No.: 459,849

Related U.S. Application Data

[63] Continuation of Ser. No. 164,139, July 19, 1971, abandoned.

[30] Foreign Application Priority Data

July 17, 1970  Japan.............................. 45-62682

[52] U.S. Cl. .................... 260/621 R; 260/624 C; 260/619 R
[51] Int. Cl.² ....................................... C07C 214/32
[58] Field of Search ......... 260/624 C, 621 R, 619 R

[56] References Cited
UNITED STATES PATENTS

| | | | |
|---|---|---|---|
| 2,448,942 | 9/1948 | Winkler et al. | 260/621 |
| 3,716,589 | 2/1973 | Kotanigawa et al. | 260/621 R |
| 3,855,318 | 12/1974 | Nakajima et al. | 260/62 R |
| 3,857,899 | 12/1974 | Tasaka | 260/621 R |

FOREIGN PATENTS OR APPLICATIONS

| | | | |
|---|---|---|---|
| 2,127,083 | 12/1971 | Germany | 260/621 R |
| 717,588 | 10/1954 | United Kingdom | 260/621 R |
| 1,131,940 | 10/1968 | United Kingdom | 260/621 R |

OTHER PUBLICATIONS

Hougen, "Chemical Process Principles" pp. 902–905.
J. Amer Chem. Society, vol. 69, pp. 2559–2560 (1947).
Catalyst Handbook, pp. 22–23 (1970).
Greg et al., "J. Chem. Soc." pp. 3946–3948 and 3954.
Linsen, Physical and Chemical Aspects of Adsorbents and Catalyst, p. 274.
Ind. Eng. Chem. Prod. Research & Development, Thomas "Catalytic Processes & Proven Catalyst", pp. 246–252 (1970).

Primary Examiner—James O. Thomas, Jr.
Assistant Examiner—W. B. Lone
Attorney, Agent, or Firm—Robert E. Burns; Emmanuel J. Lobato; Bruce L. Adams

[57] ABSTRACT

In a process for methylation of phenols having at least one ortho-positioned hydrogen with methanol in the vapor phase, the methylation is catalytically carried out in the presence of a manganese oxide catalyst to produce ortho-methylphenols.

4 Claims, No Drawings

PROCESS FOR PRODUCING ORTHO-METHYLPHENOLS

This is a continuation, of application Ser. No. 164,139, filed Jul. 19, 1971 now abandoned.

BACKGROUND OF THE INVENTION

This invention relates to a process for selectively alkylating phenols and more particularly to a process for introducing a methyl group into an ortho-position of a phenol. The description of a position is with respect to a hydroxyl group of the phenol.

Ortho-methylphenols, particularly 2, 6-xylenol, are important compounds which are recently attracting wide interest as raw materials of synthetic resins such as polyphenylene-oxide (hereinafter referred to simply as PPO). Furthermore, 2, 3, 6-trimethylphenol is important as an intermediate product for synthesis of 2, 3, 6-trimethyl-hydroquinone, a raw material for vitamin E.

Although 2, 6-xylenol is contained in coal or petroleum tar, the recovery thereof is difficult, and, accordingly, various methods of synthesis thereof have been studied.

As one of the various syntheses, there is a process for the methylation of phenol in which a phenol having at least one orthopositioned hydrogen is caused to react with methanol in the vapor phase in the presence of a catalyst which is selected from various metal oxides. For example, such a process as that wherein phenol is subjected to methylation with methanol in the vapor phase in the presence of a magnesium oxide catalyst is known.

It is generally considered that magnesium oxide catalysts are those having advantageous characteristic features, because the yield of or selectivity to methylphenols is more favorable than that in the case where the other widely known metal oxide catalysts are used. However, in the process in which magnesium oxide is employed as a catalyst, as far as we know, a high temperature and high pressure are required, and, further, the life of the catalyst is not very long.

In order to solve the difficulties as mentioned above, various improvements have been proposed, but sufficiently satisfactory results cannot be obtained by conventional improvements. For example, they are accompanied by disadvantages such as high cost of the catalyst or the continued need for high temperature and pressure even if the life of the catalyst is prolonged.

SUMMARY OF THE INVENTION

It is an object of the present invention to solve the above-mentioned problems, and this object is attained by catalytically effecting vapor-phase methylation of phenols with methanol in the presence of a manganese oxide catalyst.

According to the present invention, briefly summarized, there is provided a process for producing ortho-methylphenols in which methylation of phenol having at least one ortho-positioned hydrogen with methanol in vapor phase is catalytically carried out in the presence of a manganese oxide catalyst.

The nature, details, and utility of the invention will be more clearly apparent from the following detailed description beginning with general considerations and concluding with specific examples of practice constituting preferred embodiments of the invention and another example for reference.

DETAILED DESCRIPTION

When an oxide of manganese is employed as the catalyst in the process of the present invention, the problems or disadvantages accompanying the use of magnesium oxide as mentioned above can be solved or eliminated.

For example, the reaction conditions become remarkably mild in the process of this invention: even a reaction temperature lower by from 100° to 350°C than that in case where a magnesium oxide catalyst is used is sufficient for the process of this invention, and the reaction can also be carried out with the manganese oxide catalysts of the present invention at a temperature range of from 250° to 500°C; and, further, atmospheric pressure is sufficient for the reaction pressure.

As a result, there is little decomposition of methanol, which is the alkylating agent, and, production of hydrocarbons due to decomposition of phenol is also not observed. Accordingly, the yield and selectivity of methylphenols becomes very favorable. Particularly, the selectivity of orthomethylation is substantially 100 per cent. That is, the orthomethylation of phenols according to this invention in such a low temperature range as mentioned above occurs substantially exclusively, even if the phenols have unsubstituted positions, i.e., meta- and para- positions which can be methylated.

Therefore, even when a starting material is phenol itself, both ortho-positions of the phenol can be methylated in a high yield while excluding completely the production of meta- and/or paramethylphenol. This result is valuable in itself and particularly advantageous in the case where 2, 6-xylenol for PPO resin is produced, because it is generally considered that the thermal resistance of PPO resin deteriorates when meta- and/or paramethylphenol is present in the 2, 6-xylenol starting material.

Furthermore, the life of the catalysts of this invention is also remarkably improved. The catalytic activity thereof is maintained under continuous methylation for several days without loss of the activity. In view of the higher activity of the manganese oxide catalyst, re-use thereof is possible. Accordingly, since the manganese oxide catalysts have a long life as mentioned above, and are inexpensive as compared with conventional catalysts, orthomethylphenols can be advantageously produced on an industrial scale by the use of the catalyst of this invention.

These features of manganese oxide catalysts are believed unexpected, since it was heretofore believed that manganese oxide catalysts had no particularly desirable characteristics as shown in Japanese Patent Publication No. 653/1970.

The manganese oxide having such advantageous effects as mentioned above and employed in the process of this invention may be in various oxidation degree attained by adjusting or arranging the catalyst in accordance with a suitable process, and, further, the catalyst may be supported or not supported on a suitable carrier.

A suitable manganese oxide such as that described hereinbelow can be employed in the process of the present invention.

1 A manganese oxide on the market such as manganese dioxide.

2. A manganese oxide obtained by thermal decomposition of a manganese salt in a reducing atmosphere, for example, in a methanol atmosphere or pyrolysis of manganese salts such as manganese nitrate, manganese carbonate, manganese sulfate, and manganese oxalate, or 3. A manganese oxide prepared by the pyrolysis of a precipitate obtained by causing any of the above described manganese salts to precipitate with ammonia, urea, sodium hydroxide, or the like.

The manganese oxides thus obtained may be employed for the catalyst of the present invention after baking or without baking. The baking of these manganese oxides may be carried out within a considerably wide temperature range, but it is desirable to bake each oxide at a temperature above that which corresponds to the methylation temperature to which the manganese oxide is subjected, for example, above 300°C and it is particularly preferable to bake the oxide at a temperature ranging from 400° to 1500°C in order to achieve the improvement of catalytic activity. The activity of a manganese oxide baked at a temperature above 950°C is high, and, in this case, it was confirmed by X-ray diffractometry that the manganese oxide was in the form of tri-manganese tetroxide.

The baking of a manganese oxide may be carried out in a reacter prior to the reaction, and, according to circumstances, the baking may be carried out concurrently with, for example, the reductive decomposition of the above-mentioned manganese salts in the presence of a reaction material.

As a carrier for the catalyst of the present invention, alumina silica, silica-alumina, titania, zirconia, magnesia, activated carbon, or the like may be employed, and a suitable molding method such as extrusion molding, tabletting, and the like may be adopted for shaping the carried catalyst.

The manganese oxide catalyst of the present invention maintains its high catalytic activity without losing its activity even under continuous methylation for several days. However, after a long period of operation, the relative activity of the catalyst gradually deteriorates due to a deposition of carbon. When this occures, the catalyst can be easily regenerated by oxidizing it with oxygen or air.

As the phenols to be methylated, there are phenols each of which has at least one ortho-position which can be methylated, and the positions other than either or both of the ortho-positions may be those which can be methylated or not methylated. As such phenols as mentioned above, there are those each having a condensed aromatic ring, such as, for example, naphthols, as well as a phenol represented by the following general formula,

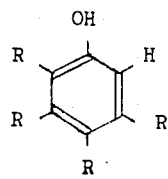

in which each R is hydrogen or monovalent substituent such as, for example, methyl, phenyl, or methyl-substituted phenyl.

As specific examples of such phenols as mentioned above, there are phenol, O-cresol, m-cresol, p-cresol, xylenols other than 2, 6-xylenol such as, 2,3-xylenol, 2,4-xylenol, and 2, 5-xylenol, 2, 3, 4-trimethylphenol, 2, 3, 5-trimethylphenol, 3, 4, 5-trimethylphenol, or bisphenols such as bisphenol A, and bisphenol F.

This vapor-phase methylation of phenols with methanol can be carried out by causing the phenols (singly or mixtures) to contact continuously or discontinuously, in a vapor phase, a manganese oxide catalyst in a fixed or non-fixed bed together with methanol and, if necessary, a diluent.

In order to obtain an ortho-methylated product in its highest yield, it is advantageous to employ at least from 1 to 30 moles of methanol, preferably from 5 to 15 moles of methanol for each othoposition of the phenol to be methylated. The highest yield of the ortho-methylated product is obtained in the above higher ratio, that is, from 5 to 15 moles of methanol per mole of the phenol. To our surprise, almost no 2,4,6-trimethylphenol and the other highly methylated phenols are produced even with such a high ratio of methanol to phenol as mentioned above. Most of the excess methanol used is taken out unchanged into its reaction product and accordingly, the methanol can be recovered therefrom and re-used.

The vapor from a reactor is condensed by an ordinary method and the product is separated in accordance with a common process such as, for example, crystallization or distillation.

Since the reaction proceeds smoothly under atmospheric pressure, a pressure vessel is not required. Furthermore, there is no danager due to the adoption of a high pressure. It is to be noted, however, that the reaction of the present invention will proceed and may be carried out under a pressure higher or lower than atmospheric pressure.

The reaction can be carried out under various reaction conditions including temperature, pressure, liquid hourly space velocity of reactant, contacting period of reactant with catalyst, length of catalyst bed, and the like. The effects attained by changing these reaction conditions are determined in accordance with technical considerations of related reactions. For instance, the reaction is generally carried out at a temperature of from 250° to 500°C. The reason for this is that when the reaction temperature is less than 250°C, the reaction rate is too low and it is undesirable from a practical technical viewpoint. On the other hand, in the case when the reaction temperature is much above 500°C, the rate of decomposition of the methanol is too great and, accordingly, is unfavorable from an economical viewpoint. Furthermore, the supplyrate of the reactants is generally 0.5 – 5 in terms of liquid hourly space velocity (hereinafter referred to simply as LHSV) and is determined in connection with the reaction temperature. In this case, LHSV corresponds to that of a catalyst volume with respect to the total quantity of a mixture of methanol and phenols.

In order to indicate still more clearly the nature and utility of the invention, the following specific examples of practice constituting preferred embodiments of the invention and results, together with a comparison example, are set forth, it being understood that these examples are presented as illustrative only, and that they are not intended to limit the scope of the invention.

Comparison Example

This example is presented for the purpose of comparing the catalytic activity of manganese oxide with that of magnesium oxide at a set temperature of from 300° to 500°C.

The magnesium oxide catalyst was prepared by adding a small amount of water to reagent grade magnesium oxide produced by WAKO JUNYAKU CO., kneading the resulting mixture, subjecting the resulting mixture to extrusion molding, drying, and baking at a temperature of 500°C.

35 cc. of the catalyst thus obtained was used for the reaction, which was carried out under atmospheric pressure. The reaction equipment comprised a vessel containing a solution of methanol and phenol and a metering pump for supplying the material to a reaction tube including a vaporizer and having an inner diameter of 21 mm, from the vessel through a glass tube. The vaporizer was surrounded by an electric heater maintained at a temperature of 180°C, and the reaction tube connected to the vaporizer was heated by an electric furnace to maintain the reaction temperature. The product vapor thus obtained from the reactor was introduced into a water-cooled condenser to receive the vapor.

The resulting distillate was analyzed by a gas-chromatographic method. In this and the following examples, all the percentages are in mole percent.

In the present reaction, the ratio of phenol to methanol was maintained at 1 : 10. With respect to the liquid space velocity, 1 cc. of the solution consisting of methanol and phenol was introduced into this reaction system relative to 1 cc. of the catalyst.

In the present example, in the case where the reaction temperature was lower than 350°C, no reaction could be observed. In the case of a reaction temperature of 400°C, the conversion of phenol was 17.1%, and the selectivity to ortho-cresol was 100%. Further, in the case of a reaction temperature of 500°C, the conversion of phenol was 81.1%, the selectivity to o-cresol was 55.7%, and the selectivity to 2, 6-xylenol was 44.3%. In this case, 3.7% of the methanol was decomposed.

EXAMPLE 1

A catalyst used in this example was prepared by adding a suitable amount of water to manganese dioxide sold on the market (electrolyzed manganese dioxide produced by TEKKOSHA). The mixture thus obtained was thoroughly kneaded to obtain an extrudable paste, which was then subjected to extrusion molding, and the substance thus molded was dried and baked at a temperature of 450°C for 3 hours.

A reaction was carried out under conditions similar to those of the comparison Example and at a reaction temperature of 375°C. The conversion of phenol was 89.8%, the selectivity to ortho-cresol was 47.9%, and the selectivity to 2, 6-xylenol was 52.1%. In this case, 2.8% of the methanol was decomposed.

EXAMPLE 2

A catalyst prepared in a manner similar to that in Example 1 was baked at a temperature of 1,000°C for 3 hours, and with this baked catalyst, a reaction was carried out at a LHSV of 2.61.

At a reaction temperature of 400°C, the conversion of phenol was 82%, the selectivity to o-cresol was 61%, and the selectivity to 2, 6-xylenol was 39%. In this case, 2.3% of the methanol was decomposed.

EXAMPLE 3

Manganese nitrate hexahydrate was dissolved in water and aqueous ammonia was dropped therein to thereby to obtain a precipitate of manganese hydroxide. The manganese hydroxide was thermally decomposed to obtain a corresponding oxide, and then a suitable amount of water was added thereto. The mixture thus obtained was extrusion molded. The molded substance was dried and then baked at a temperature of 450°C for 3 hours to prepare a catalyst.

A reaction was carried out by employing the resulting catalyst in a similar manner as in Example 1. At a reaction temperature of 375°C, the conversion of phenol was 90%, the selectivity to ocresol was 43.3%, and the selectivity to 2,6-xylenol was 56.7%. In this case, 4.0% of the methanol was decomposed.

EXAMPLE 4

Manganese nitrate hexahydrate was dissolved in water, and an excess of urea was added thereto. The resulting mixture was subjected to so-called urea homogeneous precipitation by heating the mixture in a water bath.

The resulting precipitate was filtrated and thermally decomposed to obtain an oxide, and the oxide was extrusion molded. The molded substance was dried and then baked at a temperature of 450°C for 3 hours to prepare a catalyst.

A reaction was carried out by employing the resulting catalyst similarly as in the above Example.

At a reaction temperature of 370°C, the conversion of phenol was 80%, the selectivity to o-cresol was 44.5% and the selectivity to 2, 6-xylenol was 55.5%. In this case, 2% of the methanol was decomposed.

EXAMPLE 5

In this Example, a catalyst was prepared by subjecting manganese oxide to methanol reduction at the reaction temperature to obtain manganese oxide containing a large quantity of MnO. A suitable quantity of water was added thereto, and the resulting substance was extrusion molded. The molded substance was dried and baked at a temperature of 450°C for 3 hours.

At a reaction temperature of 370°C, the conversion of phenol was 98.2%, the selectivity to o-cresol was 17.5%, and the selectivity to 2, 6-xylenol was 82.5%. In this case, 4% of the methanol was decomposed and lost.

EXAMPLE 6

In this Example, a reaction of m-cresol and methanol was carried out by employing the same catalyst as in Example 2 in such a manner that the ratio of m-cresol to methanol was 1 to 10, and the LHSV was 1.

At a reaction temperature of 375°C, the conversion of m-cresol was 100%, the selectivity to 2, 5-xylenol + 2, 3-xylenol was 8.7%, and the selectivity to 2, 3, 6-trimethylphenol was 91.3%. In this case, 9% of the methanol was decomposed.

EXAMPLE 7

A reaction was carried out by the procedure in Example 1 except for adjusting the baking temperature to 350°C. The results of the reaction were as follows.

| | |
|---|---|
| Loss of Methanol | 3.6 % |
| Conversion of Phenol | 55.6 % |

-continued

| | |
|---|---|
| Selectivity to o-Cresol | 61.6 % |
| Selectivity to 2,6-Xylenol | 38.4 % |
| Selectivity to the Other Products | 0 % |

The results of the above Examples are summarized in the following Table.

lytic active of which essentially consists of a pre-baked trimanganese tetroxide previously baked at a temperature in the range 950°C to 1500°C.

2. A process according to claim 1 in which said phenol is selected from the group consisting of phenol, O-cresol, m-cresol, p-cresol, 2, 3-xylenol, 2, 4-xylenol, 2, 5-xylenol, 2, 3, 4-trimethylphenol, 2, 3, 5-trimethylphenol, 3, 4, 5-trimethylphenol, and bisphenol A.

3. A process according to claim 1 in which the quantity of said methanol is from 1 to 30 moles per ortho-position of the phenol to be methylated.

4. A process according to claim 1 for producing 2, 6-xylenol which comprises reacting a phenol selected from the group consisting of phenol and O-cresol with from 1 to 30 moles of methanol per mole of ortho-phenol in contact with a catalyst composed essentially of trimanganese tetroxide in vapor phase at a temperature of from 250° to 500°C.

| Item | Camparison Example | Example 1 | Example 2 | Example 3 | Example 4 | Example 5 | Example 6 | Example 7 |
|---|---|---|---|---|---|---|---|---|
| Catalyst | MgO | Manganese Oxide | " | " | " | " | " | " |
| Process for Preparation | From Its Oxide Baked at 500°C | From Manganese Dioxide Baked at 450°C | From Manganese Dioxide Baked at 1000°C | Precipitation Mn(NO$_2$)$_2$.6H$_2$O with Ammonia, Baked at 450°C | Precipitating Mn(NO$_2$)$_2$.6H$_2$O with Urea, Baked at 450°C | Manganese Dioxide is subjected to Reduction by Methanol, Baked at 450°C | Same as in Example 2 | Same as in Example 1 Baked at 350° |
| Reaction Temperature (°C) | 500 | 375 | 400 | 375 | 370 | 370 | 375 | 375 |
| L H S V (l/l hr) | 1 | 1 | 2.61 | 1 | 1 | 1 | 1 | 1 |
| Methanol Loss (%) | 3.7 | 2.8 | 2.4 | 4.0 | 2.0 | 4.0 | 9.7 | 3.6 |
| Conversion of Phenol (%) | 81.1 | 89.8 | 82.0 | 90 | 80 | 98.2 | m-Cresol 100 | 55.6 |
| Selectivity to o-Cresol (%) | 55.7 | 47.9 | 61.0 | 43.3 | 44.5 | 17.5 | 2.3- and 2.5-xylenol 8.7 | 61.6 |
| Selectivity to 2,6-xylene (%) | 44.3 | 52.1 | 39.0 | 56.7 | 55.5 | 82.5 | 2.3,6-tri-methylphenol 91.3 | 38.4 |
| Selectivity to Other Products (%) | 0 | 0 | 0 | 0 | 0 | 0 | 0 | 0 |

As is apparent from the above results and detailed description, ortho-methylation can be selectively carried out by the use of the manganese oxide catalyst of the present invention under milder conditions than those under which a conventional catalyst is employed.

I claim:

1. A process for the ortho-methylation of phenols selected from the group consisting of phenol, o-cresol, m-cresol, 2,3-xylenol, and 2,5-xylenol with methanol in the vapor phase, to produce o-methylphenols which comprises contacting the vaporized phenol with methyl alcohol at a temperature in the range 250°C to 500°C in the presence of an orthomethylating catalyst, the catalytic active of which essentially consists of a pre-baked trimanganese tetroxide previously baked at a temperature in the range 950°C to 1500°C.